United States Patent
Landolina

(10) Patent No.: US 11,383,005 B2
(45) Date of Patent: Jul. 12, 2022

(54) IN-SITU CROSS-LINKABLE POLYMERIC COMPOSITIONS AND METHODS THEREOF

(71) Applicant: Cresilon, Inc., Brooklyn, NY (US)

(72) Inventor: Joseph A. Landolina, Pine Bush, NY (US)

(73) Assignee: Cresilon, Inc., Brooklyn, NY (US)

( * ) Notice: Subject to any disclaimer, the term of this patent is extended or adjusted under 35 U.S.C. 154(b) by 0 days.

(21) Appl. No.: 17/084,518

(22) Filed: Oct. 29, 2020

(65) Prior Publication Data

US 2021/0290817 A1 Sep. 23, 2021

Related U.S. Application Data

(63) Continuation of application No. 15/611,418, filed on Jun. 1, 2017, now Pat. No. 10,850,003, which is a continuation of application No. 15/266,813, filed on Sep. 15, 2016, now Pat. No. 9,687,584, which is a continuation of application No. 14/357,342, filed as application No. PCT/US2012/064670 on Nov. 12, 2012, now abandoned.

(60) Provisional application No. 61/559,110, filed on Nov. 13, 2011.

(51) Int. Cl.
*A61L 26/00* (2006.01)
*A61L 24/00* (2006.01)
*C08L 5/04* (2006.01)

(52) U.S. Cl.
CPC ......... *A61L 26/0052* (2013.01); *A61L 24/001* (2013.01); *A61L 26/0014* (2013.01); *A61L 26/0023* (2013.01); *A61L 26/0066* (2013.01); *C08L 5/04* (2013.01); *A61L 2400/04* (2013.01)

(58) Field of Classification Search
None
See application file for complete search history.

(56) References Cited

U.S. PATENT DOCUMENTS

| | | | |
|---|---|---|---|
| 4,524,064 A | 6/1985 | Nambu | |
| 4,956,350 A | 9/1990 | Mosbey | |
| 5,034,324 A | 7/1991 | Shinozaki et al. | |
| 5,670,169 A | 9/1997 | Cornell et al. | |
| 5,836,970 A * | 11/1998 | Pandit | A61L 15/225 606/213 |
| 6,150,581 A | 11/2000 | Jiang et al. | |
| 6,200,595 B1 | 3/2001 | Motoyashiki et al. | |
| 6,391,294 B1 | 5/2002 | Dettmar et al. | |
| 6,414,033 B1 | 7/2002 | Sceusa | |
| 7,112,713 B2 | 9/2006 | Sceusa | |
| 9,687,584 B1 | 6/2017 | Landolina | |
| 10,850,003 B2 | 12/2020 | Landolina | |
| 2002/0032488 A1 | 3/2002 | Brekke et al. | |
| 2003/0206958 A1 | 11/2003 | Cattaneo et al. | |
| 2005/0203058 A1 | 9/2005 | Johnson | |
| 2005/0240137 A1 | 10/2005 | Zhu et al. | |
| 2007/0166351 A1 | 7/2007 | Hossainy | |
| 2008/0139694 A1 | 6/2008 | Ratcliffe | |
| 2009/0041858 A1 | 2/2009 | Jensen | |
| 2009/0087469 A1 | 4/2009 | Zhang et al. | |
| 2009/0117175 A1 | 5/2009 | Finkielsztein et al. | |
| 2009/0123509 A1 | 5/2009 | Berkland et al. | |
| 2010/0117266 A1 | 5/2010 | Takakura et al. | |
| 2011/0144229 A1 | 6/2011 | Meyerhoff et al. | |
| 2011/0237539 A1 | 9/2011 | Yang et al. | |
| 2011/0251639 A1 | 10/2011 | Thomas et al. | |
| 2011/0287067 A1 | 11/2011 | Stewart | |
| 2012/0093686 A1 | 4/2012 | Kirsch et al. | |
| 2013/0039822 A1 | 2/2013 | Hasan | |
| 2013/0150883 A1 | 6/2013 | Fette et al. | |
| 2013/0261192 A1 | 10/2013 | Yang et al. | |
| 2013/0316007 A1 | 11/2013 | Ma et al. | |
| 2014/0287061 A1 | 9/2014 | Landolina | |
| 2018/0185543 A1 | 7/2018 | Landolina et al. | |

FOREIGN PATENT DOCUMENTS

| | | |
|---|---|---|
| CA | 2134635 | 5/1995 |
| CN | 1810298 | 8/2006 |
| CN | 101463144 | 6/2009 |
| CN | 101463145 | 6/2009 |
| JP | 59-139310 | 8/1984 |

(Continued)

OTHER PUBLICATIONS

Öztürk et al., J. Appl. Poly. Sci., 2006, vol. 101, pp. 1602-1609. (Year: 2006).*
48th Polymer preprints with English translation, Japan, 1999, vol. 48, No. 10, pp. 2431-2432.
Abreu et al., "Influence of the composition and preparation method on the morphology and swelling behavior of alginate-chitosan hydrogels." Carbohydrate Polymers, Mar. 2008, 74(2), pp. 283-289.
Abstract from Database WPI XP002738085; Japanese Application No. 2000-545736 (Kuraray Co. Ltd.), Jul. 4, 2000 (2 pgs.).
Abstract from Database WPI XP002738086; Japanese Application No. 2000-357854 (Kuraray Co. Ltd.), Apr. 25, 2000 (1 pg.).
Abu-Jdayil et al., "Modification of the rheological behaviour of sodium alginate by chitosan and multivalent electrolytes", Italian Journal of Food Science, vol. 25, pp. 196-201 (2013). Retrieved from the Internet. <URL: http://www.researchgate.net/profile/Basim_Abu-Jdayil/publication/237866139.

(Continued)

*Primary Examiner* — Brian Gulledge
(74) *Attorney, Agent, or Firm* — Nelson Mullins Riley & Scarborough LLP; Jane E. Remillard, Esq.; Cynthia L. Kanik

(57) ABSTRACT

A biocompatible polymeric composition for cross-linking in-situ in a wound is disclosed comprising 1) one or more polyanionic polymers such as alginates or hyaluronates, able to be cross-linked the surface of the wound and 2) one or more polycationic polymers such as chitosan or DEAE-Dextran, that assists in the solidification process as well as speeds up hemostasis without the need for applying pressure. The biocompatible polymeric composition may further comprise a cross-linking agent such as aqueous calcium chloride. The invention encompasses an initial polymeric composition, the solidified matrix cross-linked and integrated at the wound site, including the methods of using, applying, and cross-linking the composition.

9 Claims, 12 Drawing Sheets

(56) References Cited

FOREIGN PATENT DOCUMENTS

| | | |
|---|---|---|
| JP | 06-319517 | 11/1994 |
| JP | H7-188424 A | 7/1995 |
| JP | 11-318407 | 11/1999 |
| JP | 2000-116765 | 4/2000 |
| JP | 2000-186048 | 7/2000 |
| JP | 2001-81237 | 3/2001 |
| JP | 2004-041586 | 2/2004 |
| JP | 2008-507362 | 3/2008 |
| JP | 2009-537268 | 10/2009 |
| JP | 2011-218165 | 11/2011 |
| JP | 2018-183611 A | 11/2018 |
| WO | WO-94-06484 | 3/1994 |
| WO | WO-2000-012144 | 3/2000 |
| WO | WO-2004-091592 | 10/2004 |
| WO | WO-2006-005340 | 1/2006 |
| WO | WO-2006-012541 | 2/2006 |
| WO | WO-2007-015761 | 2/2007 |
| WO | WO-2007-135114 | 11/2007 |
| WO | WO-2010-117266 | 10/2010 |
| WO | WO-2011-011658 | 1/2011 |
| WO | WO-2011-075557 | 6/2011 |
| WO | WO-2013-050794 | 4/2013 |
| WO | WO-2013-071235 | 5/2013 |
| WO | WO-2014-091312 | 6/2014 |
| WO | WO-2014-169111 | 10/2014 |
| WO | WO-2016-209198 | 12/2016 |

OTHER PUBLICATIONS

Belman et al., "From the Battlefield to the Street-Experience of a Suburban Fire/EMS Agency with Chitosan Dressing," 2006, pp. 46-47.
Becker et al., Calcium alginate gel: A biocompatible and mechanically stable polymer for endovascular embolization, Journal of Biomedical Materials Research, vol. 54, pp. 76-86 (2001).
Dai et al., "Chitosan-Alginate Sponge: Preparation and Application in Curcumin Delivery for Dermal Wound Healing in Rat", Journal of Biomedicine and Biotechnology, 2009, vol. 2009, pp. 1-8.
Extended and Supplementary European Search Report for European Patent Application No. 12848403.7, dated Apr. 17, 2015. (8 pages).
Extended European Search Report for European Application No. 15896492.4 dated Jan. 28, 2019. (8 pages).
Gakkaishi, Sen-I, (Textile and Industry), 1990, vol. 46, No. 12, pp. 576-580.
Gotoh et al., "Preparation of alginate-chitosan hybrid gel beads and adsorption of divalent metal ions," Chemosphere, vol. 55, 2004, pp. 135-140.
He et al., "Study on synergistic interaction and gelation of chitosan and sodium alginate." J. Wuhan Univ. (Nat. Sci. Ed.), Apr. 2002, vol. 48, No. 2, pp. 193-196. (English Abstract only).
Hett et al., Sonoclot analysis. British Journal of Anaesthesia, vol. 75, 1995, pp. 771-776. Retrieved from the Internet. <URL:http://bja.oxfordjournals.org/content/75/6/771.full.pdf>.
Hong et al., "Accelerated wound healing by smad3 antisense oligonucleotides-impregnated chitosan/alginate polyelectrolyte complex," Biomaterials 29 (2008) 4831-4837.
Hou et al., "Studies on the Preparation of Chitosan-sodium Alginate Mixed Gel and Immobilization of Glucoamylase by Embedding Method," Journal of Chinese Institute of Food Science and Technology, 2009, 9(3) pp. 50-57. (English abstract only).
Hsu et al., "Evaluation of chitosan-alginate-hyaluronate complexes modified by an RGD containing protein as tissue engineering scaffolds for cartilage regeneration," Artificial Organs, vol. 28, No. 8, 2004, pp. 693-703.
International Preliminary Report on Patentability for International Application No. PCT/US2015/036894 dated Dec. 26, 2017. (23 pages).
International Preliminary Report on Patentability for International Application No. PCT/US2012/064670, dated May 13, 2014. (7 pages).
International Search Report (PCT/ISA/210) corresponding to Application No. PCT/US2012/064670, dated Mar. 25, 2013. (4 pages).
International Search Report and Written Opinion for International Application No. PCT/US2015/036894 dated Dec. 4, 2015. (27 pages).
International Search Report corresponding to Singapore Patent Application No. 11201402279S, dated May 18, 2015.
Ji et al., "Coaxially electrospun core/shell structured poly(L-lactide) acid/chitosan nanofibers for potential drug carrier in tissue engineering", Journal of Biomedical Nanotechnology. Oct. 2013; vol. 9, No. 10, pp. 1672-1678. Retrieved from the Internet. <URL: http://www.pubfacts.com/detail/24015496/Coaxially-electrospun-coreshell-structured-polyL-lactide-acidchitosan-nanofibers-for-potential-drug->.
Ozturk et al., "Preparation and Characterization of Ciprofloxacin-Loaded Alginate/Chitosan Sponge as a Wound Dressing Material," Journal of Applied Polymer Science, vol. 101, pp. 1602-1609 (2006).
Search Report for Russian Application No. 2018102112 dated May 12, 2019. (4 pages).
Suneris. Vetigel. May 21, 2015. [retrieved on Aug. 19, 2015]. Retrieved from the Internet. <URL: https://web.archive.org/web/20150521234157/http://www.suneris.co/vetigel/>.
Wang et al., "Chitosan-Alginate PEC Membrane as a Wound Dressing: Assessment of Incisional Wound Healing," 2002, vol. 63., No. 5, pp. 610-618.
Written Opinion corresponding to Singapore Patent Application No. 11201402279S, dated Dec. 16, 2015. (9 pages).
Written Opinion for SG Application No. 11201402279S dated Jun. 29, 2016. (7 pages).
Written Opinion of the International Searching Authority (PCT/ISA/237) corresponding to Application No. PCT/US2012/064670, dated Mar. 25, 2013. (6 pages).

* cited by examiner

R = H or $CH_2CO_2H$

| | Stops Bleeding | Easily Removable | Disinfects | Faster Healing | Soothes Wound | Seals Wound | Stand-alone |
|---|---|---|---|---|---|---|---|
| Bio-compatible Polymeric Composition | ✓ | ✓ | ✓ | ✓ | ✓ | ✓ | ✓ |
| Gauze/Bandage | | ✓ | | | | ✓ | ✓ |
| Liquid Bandage | | | ✓ | | | ✓ | ✓ |
| Clotting Agent | ✓ | | | | | | |
| Alginate Dressing | | ✓ | | | | ✓ | |
| Hydrogel | | ✓ | | ✓ | ✓ | | |
| Silver Anti-microbial | | ✓ | ✓ | ✓ | | | |

FIG. 4

IN-SITU CROSS-LINKABLE POLYMERIC COMPOSITIONS AND METHODS THEREOF

CROSS-REFERENCE TO RELATED APPLICATIONS

This application is a continuation of U.S. application Ser. No. 15/611,418, filed Jun. 1, 2017, which is a continuation of U.S. application Ser. No. 15/266,813, filed Sep. 15, 2016, now U.S. Pat. No. 9,687,584, which is a continuation of U.S. application Ser. No. 14/357,342, filed May 9, 2014, now abandoned, which is a U.S. National Stage Application under 35 U.S.C. § 371 of International Application No. PCT/US2012/064670, filed Nov. 12, 2012, which application claims the benefit under 35 U.S.C. § 119(e) of U.S. Provisional Patent Application No. 61/559,110, filed Nov. 13, 2011, the entire disclosure of each which is incorporated herein by reference.

FIELD OF THE INVENTION

The present invention relates generally to a composition using a biocompatible polymeric formulation and, in particular, to a hemophilic polymeric matrix for use in wound healing, blood coagulation, and cosmetic use.

BACKGROUND OF THE INVENTION

Wound healing is an intricate, orchestrated process involving the interactions of various cells and matrix components to first establish a provisional tissue and then remodel this while forming the mature replacement. Initially, the hemostatic platelet plug reestablishes the infection-limiting and desiccation-limiting barrier, and elicits the first wave of cellular infiltrates. This consists mainly of leukocytes that provide both innate and acquired immunity. These cells produce enzymes and biocidal molecules to eliminate microbial contamination; however, these same defense mechanisms are detrimental to the keratinocytes, fibroblasts and endothelial cells required to regenerate the lost tissue. Thus, as healing proceeds, the events and processes of the inflammatory phase need to regress.

A particular challenge is offered in the case of skin wound repair, which occurs at a contaminated surface. If a wound becomes infected, the normal healing is disrupted as the inflammatory phase becomes chronic, suppressing the regenerative phase. Further, the enzymes liberated by both the microbes and leukocytes break down the wound tissue as well as surrounding skin. Thus, it is critical to ensure proper healing to prevent infections being established by normal skin wound contaminants.

Wound healing is usually divided into three phases: the inflammatory phase, the proliferative phase, and the remodeling phase. Fibronectin has been reported to be involved in each stage of the wound healing process, particularly by creating a scaffold to which the invading cells will adhere. Initially, there is a release of many mediators to the wound site, such as fibronectin and fibrinogen. Fibronectin promotes inflammatory cell migration into the wound and debris phagocytosis by monocytes. Thereafter, angiogenesis and reepithelialization take place. At this stage, fibronectin exerts chemotactic activity on endothelial cells, and promotes epithelial cell and fibroblast migration onto the basal membrane. Fibronectin also appears to be essential in the remodeling phase where it plays a major role in the organization of collagen fibrils. The fibrillar collagen ultimately forms fibrous bundles that enhance the tissue tensile strength, leading to wound closure.

Hydrogels have typically been utilized as topical formulations for promoting the wound healing process. The gel compositions have been selected for their properties of swelling degree, biocompatibility, permeability, and swelling kinetics. Examples of such compounds have included vinyl polymers (e.g. polyacrylic acid), cellulose, and cellulose derivatives. Polyacrylic acid polymer, also referred to as carbomer, has been used because of its superiority in delivering fibronectin to skin wounds.

Naturally occurring biopolymers have applications in tissue engineering, regenerative medicine, drug delivery, medical implant, plastic surgery, and others. Such products have components including hyaluronic acid (HA), chitosan, heparin, chondroitin sulfate, alginate and other glucosamine and glycosaminoglycans, other polysaccharides, and derivatives thereof.

In combination, concentrations of fibronectin (and similar proteins) have been utilized with alginate salt to treat chronic ulcers. The dressing system has been solidified, converting the gel into fibers, by a process of freeze-drying. This procedure creates a sponge-like structure with hydrophilic properties. In the presence of fluids, the dressings can return to a gel-like state, absorbing up to 20 times their weight in wound exudate. The dressing is easily removed after the wound treatment because of its sponge-like structure and moisture retention. However, once hydrated with saline solution, the fibronectin-cellulose dressing does not provide the desired fibrous protective film on the surface of the deepithelialized human skin. Debridement is then performed upon removal of the dressing to remove any necrotic material.

Thus, problems exist in the treatment of acute and chronic wounds, including delayed healing, reduced granulation and epithelialization, and persistent wound inflammation. Compromised wound healing can result in other complications and problems, such as infection, pain, and development of chronic (non-healing) wounds.

Current needs exist in the treatment of chronic wounds which would assist healing, decrease inflammation, reduce pain, and prevent scar formation with both acute and chronic wounds. Such acute wounds that could be treated include burns, abrasions, dry skin, post-op surgical incisions, cuts, puncture wounds, blisters, insect bites, and other severe tissue injury. Chronic wound treatment might encompass slow to heal wounds including pressure ulcers, venous ulcers, diabetic foot ulcers, decubitus ulcers, and non-healing tissue injuries.

Overall, a composition is desired that will be easily applied, forming a matrix conducive to the healing of a tissue, and having anti-microbial properties. The composition may be biocompatible or quickly reacted to avoid possibilities of cytotoxicity. Further, the composition will stimulate and maximize wound healing while providing a controlled method for providing thin and thick layers of a solidified wound dressing, as desired.

Indirect effects may include reduced need for medical procedures such as debridement, decreased hospitalization time, reduced postoperative recovery times, shortened return interval to daily functions and work, and reduced overall treatment costs. Desirably, these improvements to wound healing, including application and method of use, will be valuable in treating and repairing various tissue(s).

SUMMARY OF THE INVENTION

The following invention is a biocompatible polymeric composition that is a gelatinous wound healing and hemostatic matrix able to be formed and solidified both internally and externally.

In one embodiment of the invention, the biocompatible polymeric composition comprises 1) one or more than one polyanionic polymer and 2) one or more than one polycationic polymer. In one embodiment of the invention, the one or more than one polyanionic polymer includes at least one cross-linkable polyanionic polymer. In another embodiment of the invention, the one or more than one polyanionic polymer includes at least one cross-linkable polyanionic polymer and at least one non-cross-linkable polyanionic polymer.

In one embodiment of the invention, the biocompatible polymeric composition comprises a mixture of 1) one or more than one polyanionic polymer able to be formed on the surface of a wound and 2) one or more than one polycationic polymer that assists in the solidification process as well as speeds up blood clotting. In another embodiment of the invention, the biocompatible polymeric composition comprises a mixture of 1) one or more than one polyanionic polymer able to be formed on the surface of a wound; 2) one or more than one polycationic polymer that assists in the solidification process as well as speeds up blood clotting; and 3) a cross-linking mist that cross-links the gel in the wound while disinfecting the surrounding area.

In one embodiment of the invention, the one or more than one polyanionic polymer comprises alginates or hyaluronates. In one embodiment of the invention, the one or more than one polycationic polymer comprises chitosan. In one embodiment of the invention, the cross-linking mist may be aqueous calcium chloride.

One or more methods of using the medical gel of the invention are also disclosed, including rapidly achieving hemostasis without the need to apply pressure, and providing a biocompatible wound healing matrix.

Various embodiments of the invention allow the formulation to be adjusted and implemented for varying the desired viscosity and pre-determined characteristic functions. In one aspect, the ratio of the polycationic polymer to the polyanionic polymer may be improved, having varying degrees of efficiency in wound healing. In another aspect, therapeutics can be added to integrate drug formulations for drug delivery options. Further, other features may encompass controlling temperature(s) and/or pressure(s) during the preparation of the medical gel, during application of the gel, and implementing a control for the elasticity or rigidity of the solidified matrix. The matrix formulation, both liquid and solidified structures, may also be dependent on anatomical and physiological measurements and conditions.

Various embodiments of the invention allow the composition to be adjusted and implemented at a first tissue site or a second tissue site, and such modification deemed obvious may be integrated and combined in varying quantities to provide for a structural matrix of any size, shape, and configuration.

DESCRIPTION OF THE DRAWINGS

FIG. 4 shows the benefits of the present invention as compared to existing technology.

DETAILED DESCRIPTION OF THE INVENTION

In the following detailed description, for purposes of explanation and not limitation, exemplary embodiments disclosing specific details are set forth in order to provide a thorough understanding of the present invention. However, it will be apparent to one having ordinary skill in the art that the present invention may be practiced in other embodiments that depart from the specific details disclosed herein. In other instances, detailed descriptions of well-known compositions and methods may be omitted so as not to obscure the description of the present invention.

Biocompatible polymeric compositions of the present invention may be used to treat external wounds as well as internal wounds. In one embodiment of the invention, the biocompatible polymeric composition may be applied to a variety of wounds. Non-limiting examples of wounds include, but are not limited to: an external laceration, an abrasion, a burn, an ocular laceration, damage to a parenchymal organ, an internal laceration, a laceration in the gastrointestinal tract, superficial cuts and scrapes, internal bleeding, an arterial bleed, a venous bleed, dental or oral bleeds and incisions. Subjects who can benefit from such wound treatment include a variety of animals including humans, mammals such as horses, sheep, cattle, hogs, dogs, cats, and marine animals such as whales, dolphins, seals, otters, fish, and reptiles such as turtles.

Figure 1:
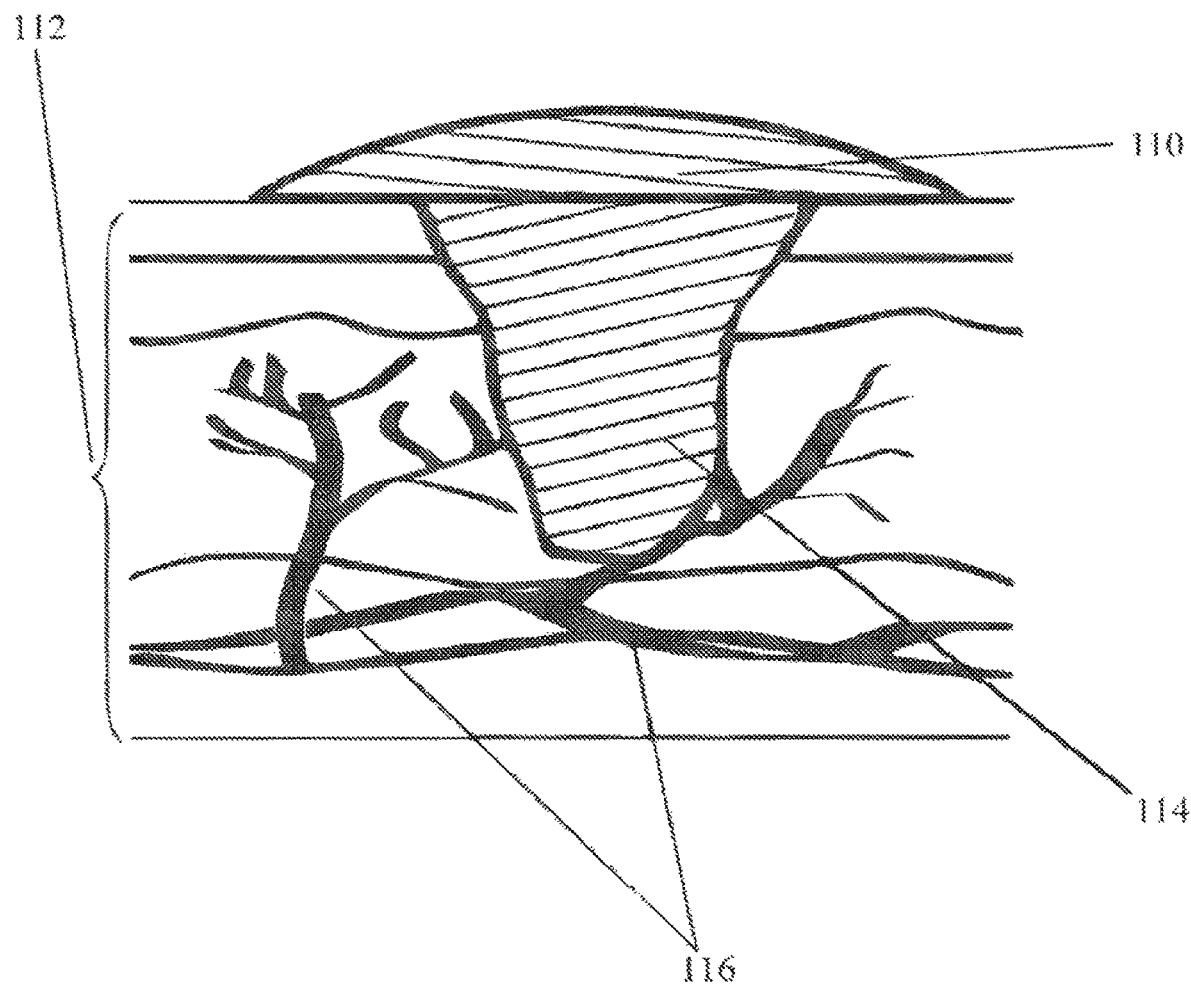
FIG. 1 is a side view of an embodiment of the present invention.

An illustration of a structural matrix in accordance with one embodiment of the invention is shown in FIG. 1. As depicted, a damaged section of tissue, wound (112), has vasculature (116) protruding throughout. A biocompatible polymeric composition (114) has been applied to the wound (112), which has been coated with protective coat (110).

Figure 2:
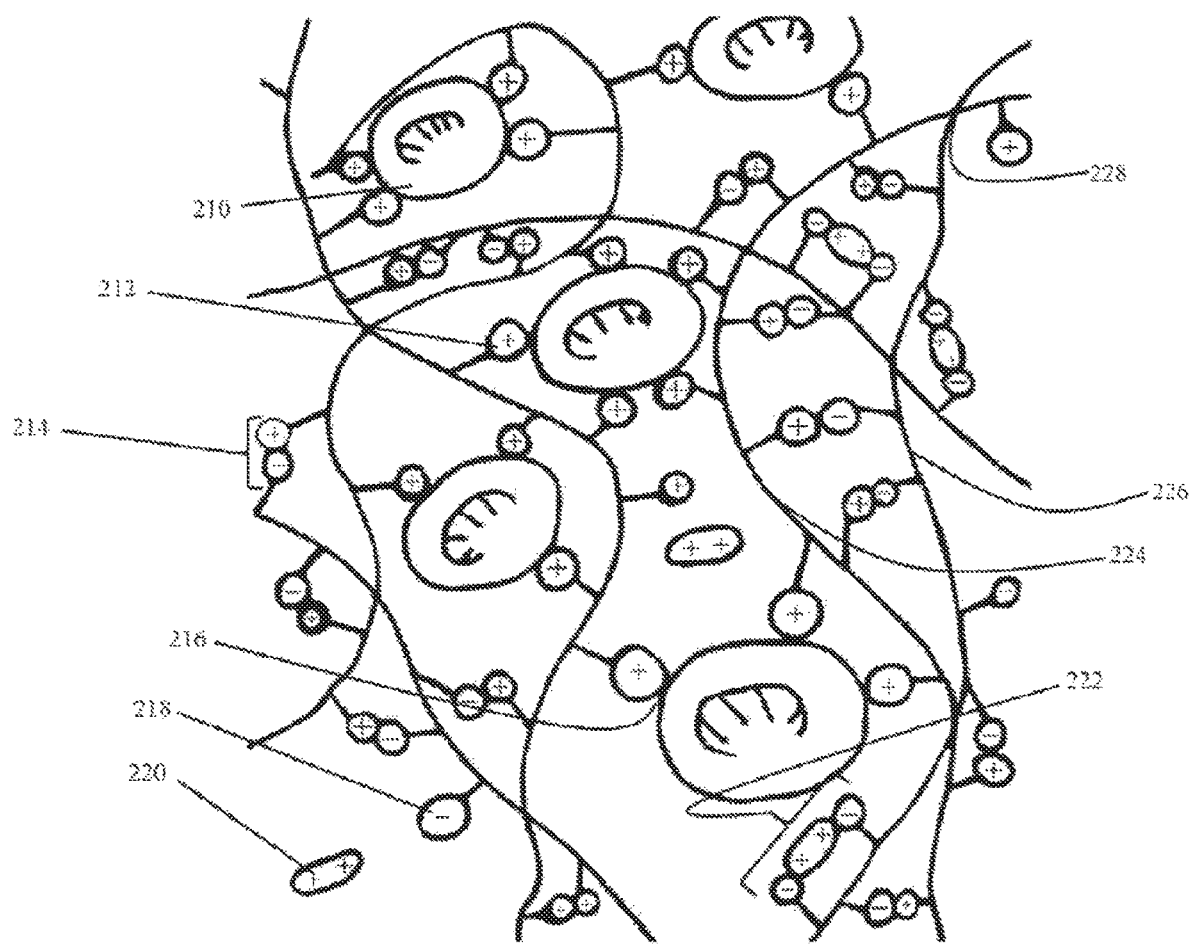
FIG. 2 is a microscopic depiction of how the present invention interacts with blood and itself.

FIG. 2 shows a magnified view of one embodiment of biocompatible polymeric composition (114), which comprises structural polymer (226) and hemophilic polymer (224). Structural polymer (226) comprises about 0.1% to 95% by total composition weight of a cross-linkable polyanionic polymer and 0% to 95% by total composition weight of a non-cross-linkable polyanionic polymer. Hemophilic polymer (224) comprises about 1% to 90% by total composition weight of a polycationic polymer. Red blood cell (210) is shown in relation to the cationic function groups (212) via a red blood cell-cationic group linkage (216).

Figure 3A:
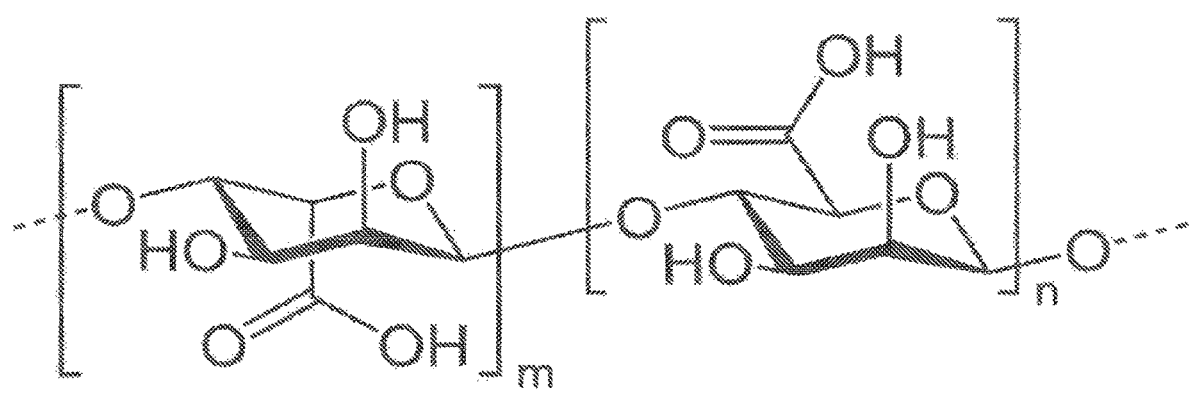
FIGS. 3A to 3I show various polymeric subunits that can be used to make up the polycationic or polyanionic polymers.
Figure 3B:
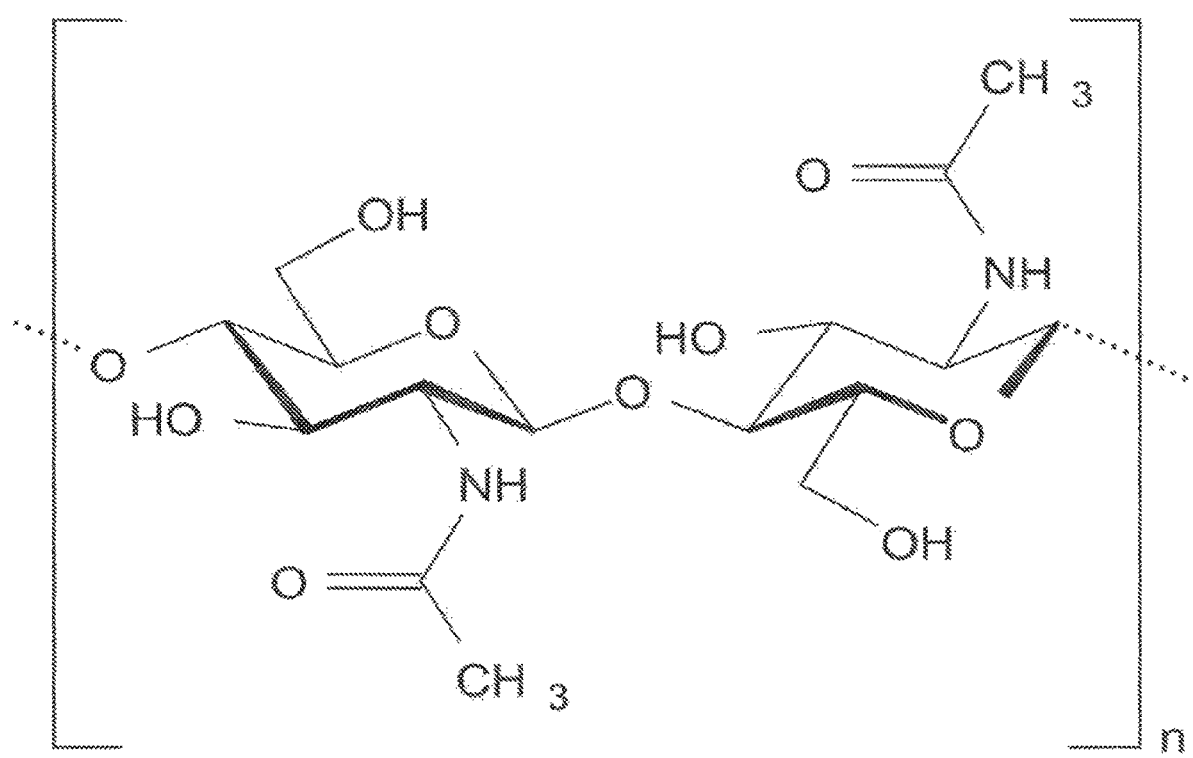
Figure 3C:
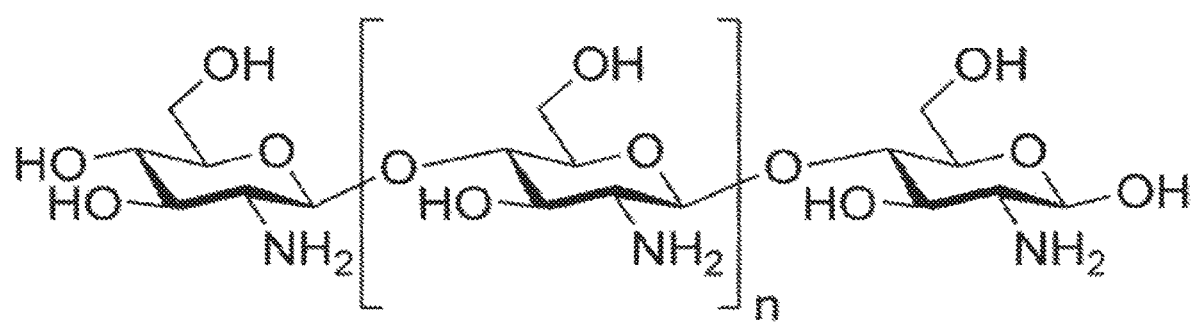
Figure 3D:
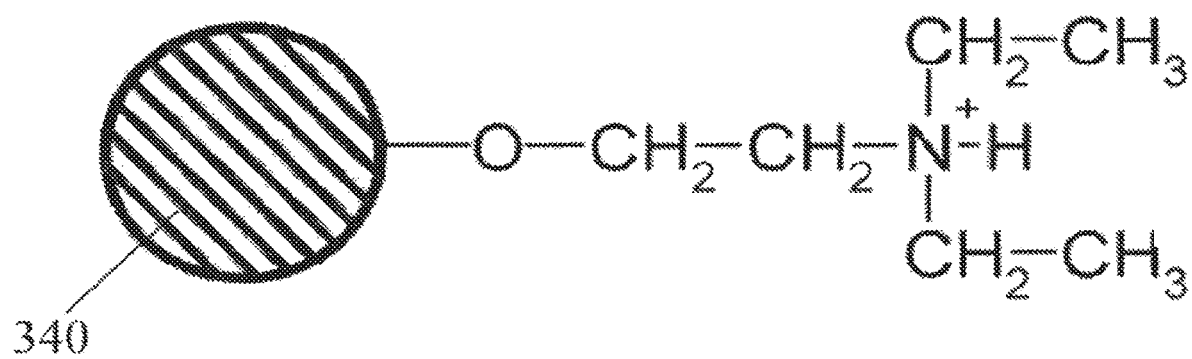
Figure 3E:
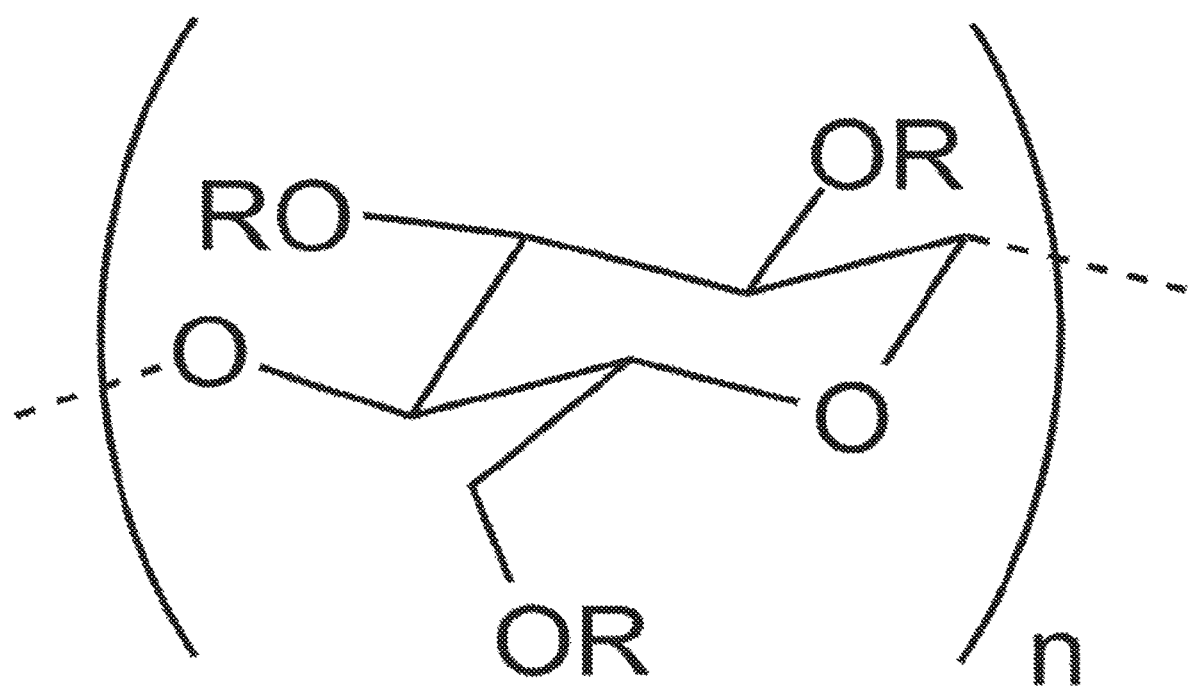
Figure 3F:
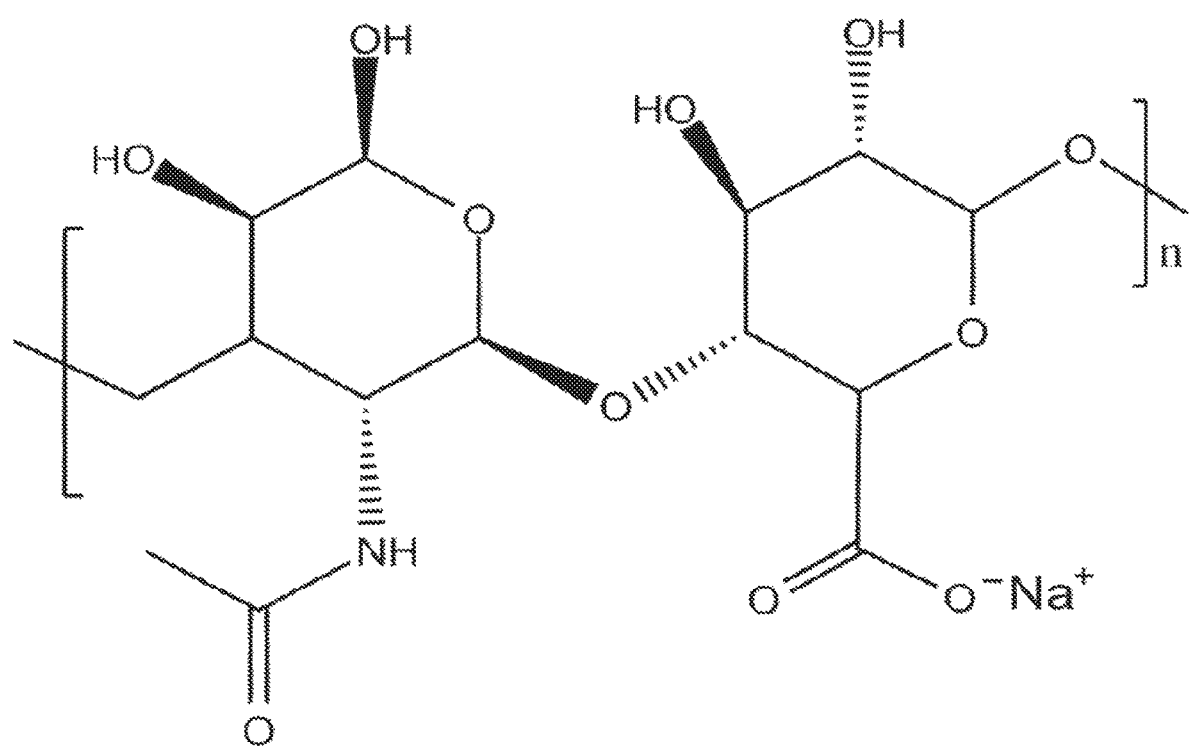
Figure 3G:
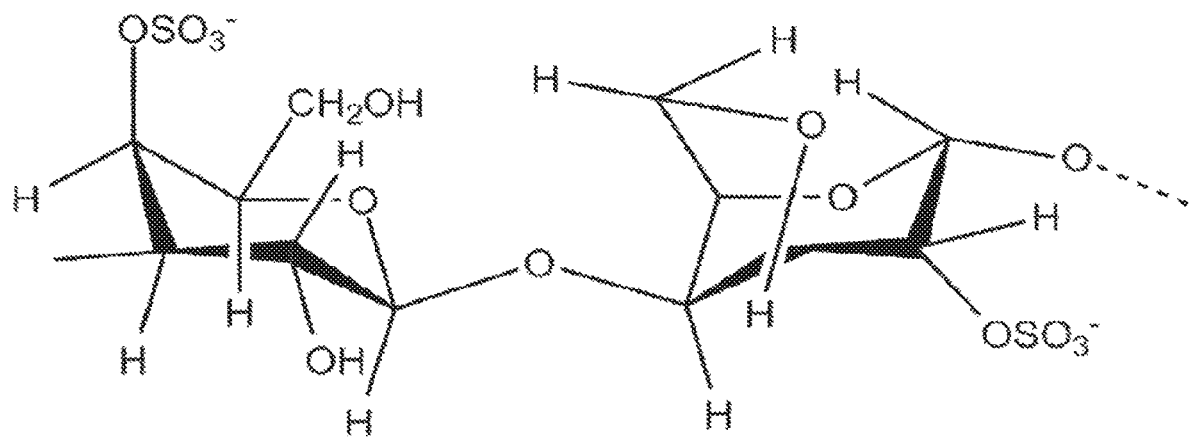
Figure 3H:
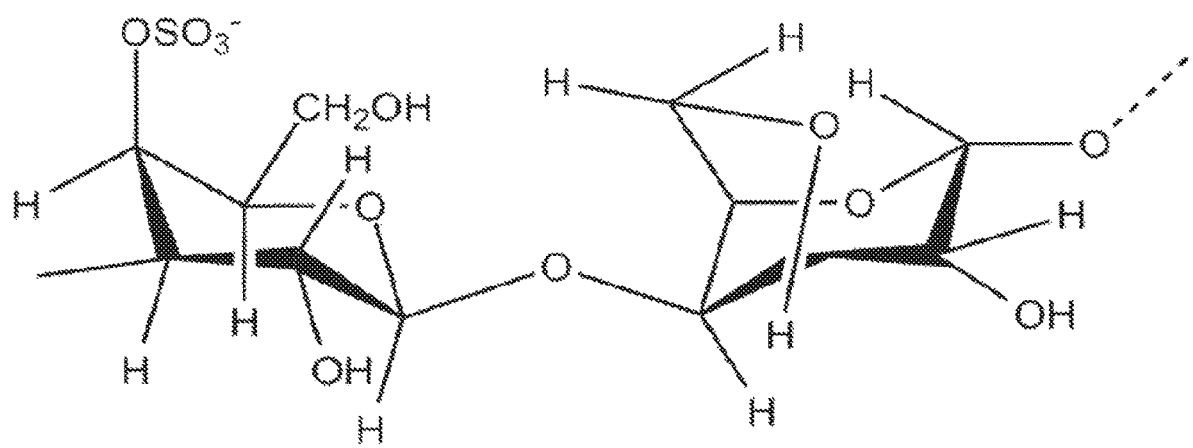
Figure 3I:
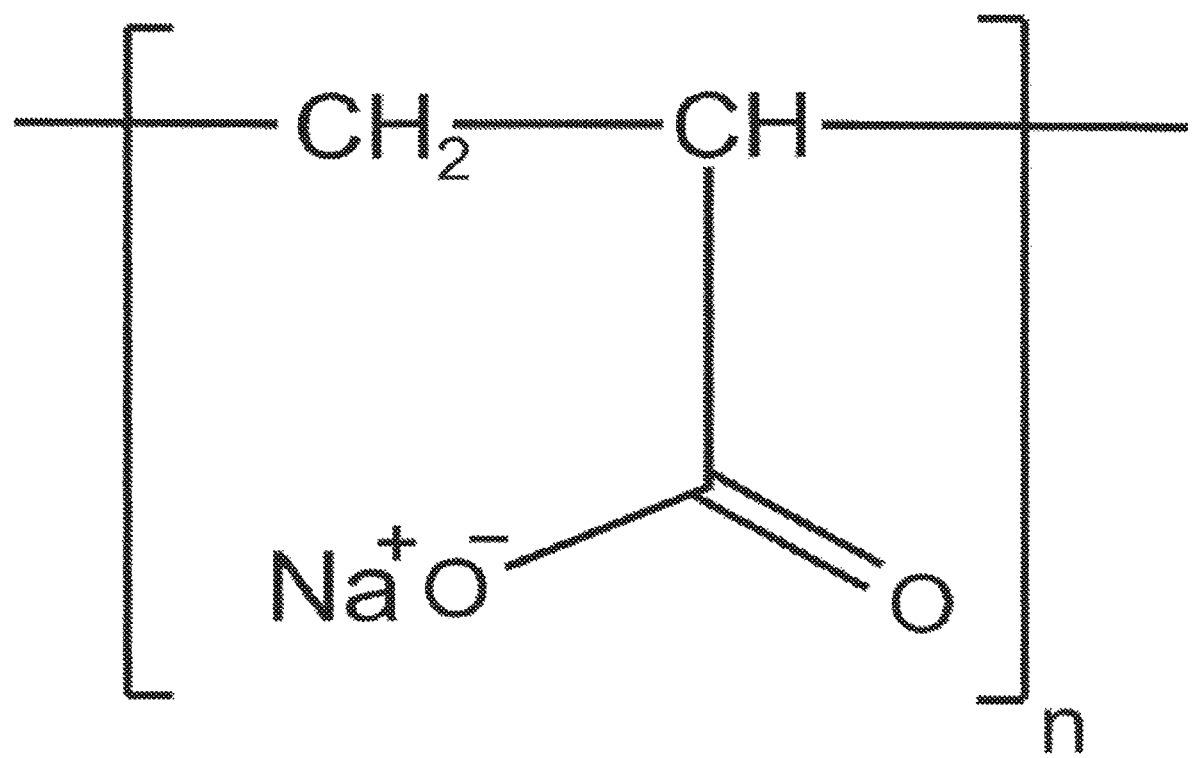

FIGS. 3A to 3I show various polymers that can be chosen as structural polymer (226) or hemophilic polymer (224). Polymers can be modified through the addition of carboxymethyl (CM) groups to gain anionic functional groups (218). FIG. 3E shows carboxymethyl cellulose. Alginate (3A), sodium hyaluronate (3F), κ-carrageenan (3G), ι-carrageenan (3H), and sodium polyacrylate (3I) are examples of polymers that would function as structural polymer (226). Likewise, chitin (3B) and chitosan (3C) are examples of polymers that would function as hemophilic polymer (224). FIG. 3D shows how any polymer (340) can be modified with a diethylaminoethyl (DEAE) group to gain cationic functional groups (212).

Biocompatible polymeric composition (114) contains about 0.1% to 99.8% by total composition weight of a solvent. In one embodiment of the invention, the solvent is ethanol. Preferably the solvent is a 5% aqueous solution of ethanol in water. Non-limiting examples of solvents include water, ethanol, amyl acetate, acetone, methyl ethyl ketone, isopropanol, and tetrahydrofuran. In solution, structural polymer (226) and hemophilic polymer (224) experience intermolecular interactions which bind them together. Cationic function groups (212) on hemophilic polymer (224) attract anionic functional groups (218) on structural polymer (226) and result in ionic cross-linking (214). Additionally, hemophilic polymer (224) and structural polymer (226) can be covalently cross-linked (228), similar to a Schiff base or azomethine linkage.

Protective coat (110) comprises 0.1% to 30% by weight of a di- or higher valent cation (220), 0% to 90% by weight of a hydrophobic polymer, and 5% to 99.9% by weight of a solvent. Protective coat (110) cross-links composition (114) by diffusing divalent cation (220) inwards, which results in divalent cation cross-linking (222) of structural polymer (226). This increases the rigidity of composition (114) and allows for better stability. Protective coat (110) can also contain hydrophobic polymers, which limit the water loss from composition (114) and improve durability. The hydrophobic polymer may be a polyurethane, nitrocellulose, a cyanoacrylate, a styrene, a polytetrafluoroethane, and a silicone, and combinations thereof. The solvent may be water, amyl acetate, acetone, methyl ethyl ketone, isopropanol, and tetrahydrofuran, and combinations thereof. The di- or higher valent cation may be $Ca^{2+}$, $Fe^{2+}$, $Fe^{3+}$, $Ag^{2+}$, $Ag^{3+}$, $Au^{2+}$, $Au^{3+}$, $Mg^{2+}$, $Cu^{2+}$, $Cu^{3+}$, and $Zn^{2+}$. In one embodiment of the invention, the cation is $Ca^{2+}$.

In one embodiment of the invention, structural polymer (226) comprises 0.1% to 5% by weight of sodium alginate and 1% to 5% by weight of sodium hyaluronate, hemophilic polymer (224) comprises 2% to 2.5% by weight of chitosan chloride, and the solvent comprises 65% to 96.9% by weight of a 5% aqueous solution of ethanol in water. In this embodiment, the composition functions as a wound healing matrix to facilitate faster tissue regeneration.

In another embodiment, structural polymer (226) comprises 2% to 5% by weight of sodium alginate and 0% to 2% by weight of sodium hyaluronate, hemophilic polymer (224) comprises 5% to 20% by weight of chitosan chloride, and the solvent comprises 73% to 93% by weight of a 5% aqueous solution of ethanol in water. In this embodiment, the composition functions as a thick gel for rapidly achieving hemostasis without the need to apply pressure. The composition can be delivered topically to the compromised blood vessel.

In another embodiment of the invention, structural polymer (226) comprises 0.1% to 4% by weight of sodium alginate and 1% to 5% by weight of a lysine-rich polypeptide, hemophilic polymer (224) comprises 5% to 25% by weight of diethylaminoethyl-dextran (DEAE-Dextran), and the solvent comprises 65% to 93% by weight of a 5% aqueous solution of ethanol in water. The biocompatible polymeric composite (114) is then cross-linked in situ by applying an aerosol mist comprising 0.1% to 1% by weight of calcium chloride, 1% to 5% by weight of nitrocellulose, and 94% to 98.9% by weight of amyl acetate. In this embodiment, the composition functions as a protective covering for cuts and scrapes that is durable and limits water loss from the wound.

In one embodiment of the invention, the biocompatible polymeric composition comprises about 3.6% by weight of sodium alginate, about 7% by weight of chitosan chloride, and about 89.4% by weight of a 5% aqueous solution of ethanol in water. This embodiment may function as a composition to treat arterial bleeds.

In one embodiment of the invention, the protective coat comprises a solution comprising about 0.1% to about 30% by weight of a di- or higher valent cation; 0% to about 90% by weight of a hydrophobic polymer; and about 5% to about 99.9% by weight of a solvent. In one embodiment of the invention, the protective coat comprises a solution comprising about 0.1% to about 1% by weight of a di-valent cation; about 1 to about 5% by weight of a hydrophobic polymer; and about 94% to about 98.9% by weight of a solvent.

In one embodiment of the invention, composition (114) is used as a carrier for a therapeutic agent such as a drug or biologic molecule. The use of composition (114) as a drug delivery system improves the efficiency of the wound healing gel. In one aspect, protective coat (110) is prepared with a salt of silver, increasing the antimicrobial properties of the gel. In one embodiment, the therapeutic agent is selected from the group consisting of: antimicrobial agents, antibiotics, hormones, proteins (such as calreticulin, thrombin, prothrombin, Factor VIII), and iodine, and combinations thereof. In one embodiment of the invention, the therapeutic agent is preferably iodine. In another embodiment of the invention, the therapeutic agent is a protein.

In one embodiment of the invention, the cross-linkable polyanionic polymer may be a polystyrene sulfonate (such as sodium polystyrene sulfonate), a polyacrylate (such as sodium polyacrylate), a polymethacrylate (such as sodium polymethacrylate), a polyvinyl sulphate (such as sodium polyvinyl sulphate), a polyphosphate (such as sodium polyphosphate), Iota carrageenan, Kappa carrageenan, gellan gum, carboxyl methyl cellulose, carboxyl methyl agarose, carboxyl methyl dextran, carboxyl methyl chitin, carboxyl methyl chitosan, a polymer modified with a carboxyl methyl group, an alginate (such as sodium alginate), a polymer containing a plurality of carboxylate groups, a xanthan gum, and combinations thereof. Preferably, the crosslinkable polyanionic polymer is an alginate, more preferably sodium alginate.

Preferably the cross-linkable polyanionic polymer comprises about 1% to about 95% by weight of the biocompatible polymeric composition; preferably the cross-linkable polyanionic polymer comprises about 5% to about 40% by weight of the biocompatible polymeric composition; preferably the cross-linkable polyanionic polymer comprises about 10% to about 30% by weight of the biocompatible polymeric composition.

In one embodiment of the invention, the non-cross-linkable polyanionic polymer may be a hyaluronate (such as sodium hyaluronate), a polynucleotide (such as RNA), a polypeptide chain having an average residue isoelectric point below 7, a glucosaminoglycan, and a proteoglycan, and combinations thereof. Preferably the non-cross-linkable polyanionic polymer is a hyaluronate, more preferably sodium hyaluronate.

Preferably the non-cross-linkable polyanionic polymer comprises about 0 to about 95% by weight of the biocompatible polymeric composition; preferably the non-cross-linkable polyanionic polymer comprises about 5 to about 25% by weight of the biocompatible polymeric composition; preferably the non-cross-linkable polyanionic polymer comprises about 0 to about 5% by weight of the biocompatible polymeric composition; preferably the non-cross-linkable polyanionic polymer comprises about 0 to about 2% by weight of the biocompatible polymeric composition;

preferably the non-cross-linkable polyanionic polymer comprises about 1 to about 5% by weight of the biocompatible polymeric composition.

In one embodiment of the invention, the polycationic polymer may be a chitosan (such as chitosan chloride), chitin, diethylaminoethyl-dextran, diethylaminoethyl-cellulose, diethylaminoethyl-agarose, diethylaminoethyl-alginate, a polymer modified with a diethylaminoethyl group, a polymer containing a plurality of protonated amino groups, and a polypeptide having an average residue isoelectric point above 7, and combinations thereof. Preferably the polycationic polymer is a chitosan, more preferably chitosan chloride. Preferably the polycationic polymer is diethylaminoethyl-dextran (DEAE-Dextran).

Preferably the polycationic polymer comprises about 1% to about 90% by weight of the biocompatible polymeric composition; preferably the polycationic polymer comprises about 2% to about 80% by weight of the biocompatible polymeric composition; preferably the polycationic polymer comprises about 2% to about 25% by weight of the biocompatible polymeric composition.

The individual components of the biocompatible polymeric composition may be stored in a variety of different containers for a variety of different applications, including for example, packets, sachets, tubes, tubs, pumps, syringes, bottles, bags, and aerosol-based spray cans. The components may be stored in containers made of a variety of materials, including for example, plastic, metal, or glass. The components may be provided in operably connected configurations, or as separate components for a user to set up prior to use.

The compositions and systems described herein may be included in a kit or article of manufacture for forming a biocompatible polymeric composition comprising one or more of: a solution comprising a polyanionic polymer; a solution comprising a polycationic polymer; a solvent; and a solution comprising a di- or higher valent cation, a hydrophobic polymer, and solvent. The kit or article of manufacture may further contain gauze, bandages, tape, brushes, spatulas, and sponges.

A number of implementations have been described. Nevertheless, it will be understood that various modifications may be made without departing from the spirit and scope of this document. In particular, for example, various compositions of the solutions have been described, but varying similar components and elements may be integrated or utilized in substitution to achieve the same or similar effect. Moreover, varying matrices may be employed to target diverse wound locations, internal or external to the dermal layers of the skin, including organ transplantation, tissue grafting, and/or various surgical incisions and lesions at any site or location external and/or internal to the body. Accordingly, other implementations are within the scope of the following claims.

Further, the studies described may utilize one embodiment of the composition to form a rigid matrix while another composition may be designed with an increased elasticity, alone or in combination. Further, the methods of mixing and formulating the composition may be performed in any order and combination so as to achieve the same or similar effects of the embedded solidified matrix, the matrix integrating the formation of naturally restructuring tissue. In one embodiment, the one or more than one polyanionic polymer is first applied to a wound and then the one or more than one polycationic polymer is applied to the said one or more than one polymeric polymer at the wound site. In one embodiment, the one or more than one polyanionic polymer is mixed with the one or more than one polycationic polymer and then the mixture is then applied to the wound. In one embodiment, the one or more than one polyanionic polymer is applied to a wound at the same time, or about the same time, that the one or more than one polycationic polymer is applied to a wound.

In one embodiment, a method of treating a wound comprises applying one or more than one polyanionic polymer to a wound and then applying one or more than one polycationic polymer to the said one or more than one polymeric polymer at the wound site. In one embodiment, a method of treating a wound comprises mixing one or more than one polyanionic polymer with one or more than one polycationic polymer and then applying the mixture to the wound. In one embodiment, a method of treating a wound comprises applying one or more than one polyanionic polymer to the wound at the same time, or about the same time, as one or more than one polycationic polymer is applied to a wound.

What is claimed:
1. A biocompatible polymeric composition comprising:
   a. 0.1% to 5% by weight of sodium alginate;
   b. 2% to 25% by weigh of chitosan; and
   c. the balance of the composition is water.
2. The biocompatible polymeric composition of claim 1, wherein the composition comprises 2% to 5% by weight of sodium alginate.
3. The biocompatible polymeric composition of claim 1, wherein the chitosan is chitosan chloride.
4. The biocompatible polymeric composition of claim 1, wherein the composition comprises 73% to 93% by weight of water.
5. The biocompatible polymeric composition of claim 1, wherein the composition forms a gelatinous matrix.
6. A container comprising the biocompatible composition of claim 1.
7. The container of claim 6, wherein the container is a packet, sachet, tube, tub, pump, syringe, bottle, bag or aerosol-based spray can.
8. The container of claim 5, wherein the container is a syringe.
9. A kit comprising the biocompatible composition of claim 1.

\* \* \* \* \*